United States Patent [19]

Schmitz

[11] Patent Number: 5,772,825
[45] Date of Patent: Jun. 30, 1998

[54] METHOD FOR MAKING AN UNDERGARMENT HAVING SIDE SEAMS

[75] Inventor: Christoph Johann Schmitz, Euskirchen-Stotzheim, Germany

[73] Assignee: The Procter & Gamble Company, Cincinnati, Ohio

[21] Appl. No.: 849,981

[22] PCT Filed: Dec. 21, 1995

[86] PCT No.: PCT/US95/16657

§ 371 Date: Jun. 20, 1997

§ 102(e) Date: Jun. 20, 1997

[87] PCT Pub. No.: WO96/19123

PCT Pub. Date: Jun. 27, 1996

[30] Foreign Application Priority Data

Dec. 22, 1994 [EP] European Pat. Off. .............. 94120377

[51] Int. Cl.$^6$ .............................. A41B 9/12; A61F 13/15; B32B 31/18; B32B 31/20

[52] U.S. Cl. ............................. 156/164; 2/402; 156/163; 156/211; 156/217; 156/226; 156/227; 156/264; 156/267; 156/292; 156/308.4; 156/443; 156/494; 156/516; 156/522; 156/538; 156/539; 156/543; 156/566; 604/396

[58] Field of Search ................................ 2/400, 401, 402, 2/403, 406; 604/385.1, 385.2, 393, 396; 156/73.1, 163, 164, 211, 217, 222, 226, 227, 264, 267, 269, 270, 292, 308.4, 443, 494, 495, 496, 510, 516, 522, 538, 539, 543, 552, 556, 562, 566, 580.1

[56] References Cited

U.S. PATENT DOCUMENTS

5,536,350 7/1996 Klemp .............................. 604/385.1 X
5,626,711 5/1997 Herrmann ........................... 156/538 X

*Primary Examiner*—Adrienne C. Johnstone
*Attorney, Agent, or Firm*—Theodore P. Cummings; Steven W. Miller; Jacobus C. Rasser

[57] ABSTRACT

A method for forming an undergarment having side seams from a two-dimensional preform comprises the steps of cutting a continuous web along transverse cut lines to form individual preforms; cutting each preform along a leg contour extending along each longitudinal side of the preform in the region of a central section, wherein each leg contour does not touch the respective longitudinal side, thus forming two gripping flaps; gripping the preform at the gripping flaps; pulling the gripping flaps outwardly away from the longitudinal sides such that the preform is doubled over along a transverse centerline and such that sealing areas in the region of back waist sections are placed in a superimposed relationship with sealing areas in the region of front waist sections; mutually connecting the sealing areas.

6 Claims, 8 Drawing Sheets

METHOD FOR MAKING AN UNDERGARMENT HAVING SIDE SEAMS

FIELD OF THE INVENTION

The invention relates to a method of making an undergarment having side seams from a two-dimensional preform.

The invention also relates to an apparatus for carrying out said method and to a preform for making such an undergarment.

BACKGROUND OF THE INVENTION

Undergarments, in particular disposable absorbent articles having side seams, are known from EP-B-0187728. These articles have butt-type or overlapping side seams which are formed by superimposing the sealing areas at the front and the back waist regions and connecting the front waist region to the back waist region by adhesive-, fusion, ultrasonic or other bonds.

It is an object of the present invention to provide a method of forming an undergarment having side seams which can be accurately produced at high speeds.

It is another object of the invention to provide an accurate and high-speed method for making an undergarment having side seams and comprising an active elastic element along at least one transverse side, for instance a pre-stretched elastic element.

It is again another object of the invention to provide an apparatus for forming an undergarment, in particular a disposable absorbent article having side seams.

SUMMARY OF THE INVENTION

A method of forming an undergarment in accordance with the present invention comprises the steps of cutting a continuous web along transverse cut lines to form individual preforms, cutting each preform along a leg contour extending along each longitudinal side in the region of a central section thereof, wherein each leg contour does not touch the respective longitudinal side, thus forming two gripping flaps, gripping the preform at the gripping flaps, pulling the gripping flaps outwardly away from the longitudinal sides such that the preform is doubled over along the transverse centerline and such that the sealing areas in the region of the back waist sections can be placed in a superimposed relationship with the sealing areas in the region of the front waist sections, and mutually connecting the sealing areas.

By cutting the leg contours in the preform such that the cut-out sections remain attached to the preform, the preform can be gripped at the cut-out sections. When the cut-out sections, or gripping flaps, are gripped at the hight of the transverse center line and are pulled outwardly, the preform is folded about its transverse centerline. The sealing areas in the front and back waist regions can in this way be accurately superimposed because the positions in which the preform is gripped on the gripping flaps are fixed at each stage of the folding process. No hand-over of the preform is necessary between for instance the application of leg- or waist elastics to the preform and the folding- and sealing step. In this way good process control is obtained which allows high speed production, for instance at speeds of 120 meters per minute or more. Furthermore, the method according to the invention allows to handle webs which are contracted by elastic elements both in the length direction of the web and in a direction transversely thereto.

The preform can comprise a single sheet of material such as a polyethylene film or a non-woven material, which can be an elastic or non-elastic non-woven material. The preform can also be a laminate of a non-woven material and a thermoplastic film, or can be formed by the combination of a liquid-pervious topsheet and a liquid-impervious backsheet between which an absorbent element is encased. Alternatively, the preform can comprise an absorbent element of the insert-type comprising a topsheet, a backsheet and an absorbent core, the insert absorbent element being connected to the preform material and optionally being detachable therefrom for disposal.

An embodiment of the method according to the invention comprises the steps of supplying a two-dimensional web or preform in a direction of transport below a rotatable supply roll having an axis of rotation located generally perpendicular to the direction of transport, gripping the web or the preform in the region of the longitudinal sides, supplying an elastic element from the supply roll extending transversely across at least a part of the width of the preform, wherein the supply roll comprises a peripheral cutting element, rotating the supply roll to engage the cutting element with the preform along the leg contours to form the gripping flaps, pulling the gripping flaps outwardly, connecting the sealing areas, and cutting off the gripping flaps.

By combining the application of the waist elastics and the cutting of the leg contours, accurate control of the position of the waist edges of the preform is obtained. By synchronising the cutting of the leg contours with application of the waist elastics, the preform or web can be maintained in a flattened state at all stages of the production process. As a result, after application of the waist elastics, other elements, such as a topsheet, core, further elastics, etc. may be accurately positioned with respect to the web and can subsequently be attached thereto.

In a method of forming an undergarment, wherein the pre-form is maintained in its flattened state at all stages of the forming process, the following steps are carried out.

First a waist elastic is applied along the leading edge of the preform. At this moment two grippers engage the longitudinal sides of the preform. Immediately following application of the waist elastic along the leading edge, the leg contours are cut by the same roll with which the waist elastic has been applied. Thereby the pull force of the grippers is transferred to the leading edge of the preform. Upon completion of the leg contours, the grippers pull both the leading edge and the trailing edges of the preform taut and counteract the gathering force of the waist elastics. Finally, after application of the elastic along the leading edge and after cutting of the leg contours, a second waist elastic is the connected along the trailing edge of the preform. At the moment the waist elastic is connected along the trailing edge, this edge is under tension by the pull force from the grippers acting on the waist sections of the preform via the gripping flaps and is prevented from being contracted by the elastic.

BRIEF DESCRIPTION OF THE DRAWINGS

The invention will be described in detail with reference to the accompanying drawings. In the drawings.

DETAILED DESCRIPTION OF THE INVENTION

The term "undergarment" is intended to mean an article which is used in combination with an absorbent element or which comprises an absorbent element as integral part thereof. The undergarment may comprise for instance a panty or pants, of woven or non-woven material, of plastic or of rubber. In the pants attachment means may be provided to accommodate a separate absorbent element. Alternatively, the pants may not comprise any means for affixation of the absorbent element, and may for instance be net-type pants for use by incontinent persons. The undergarment preferably forms a disposable absorbent article.

The term "disposable absorbent article" is intended to mean an article which is discarded after not more than a number of uses. Disposable absorbent articles comprising side seams include pull-on type baby diapers, training pants and adult incontinence briefs.

The term "two-dimensional preform" or "blank" is intend to mean a single sheet of material, a laminate of two or more sheets of material or an integral combination of topsheet backsheet and an absorbent element encased between the topsheet and the backsheet. The preform can comprise a single, liquid impermeable sheet of thermoplastic material or a liquid permeable or impermeable non-woven material. Alternatively, the preform comprises a laminate of a thermoplastic film and a layer of non-woven material on the garment-facing side. In case the preform comprises a combination of a backsheet, a topsheet and a core interposed between the topsheet and the backsheet, the topsheet may be co-extensive with the backsheet or may be of smaller dimensions, such that the topsheet material does not overlap with the sealing areas.

In a preferred embodiment the preform comprises elastic elements, for instance along the leg regions, the waist regions or along regions that are to form the side seams. The elastic elements may contact or gather the preform (active elastic elements) or may be affixed to the preform in their relaxed state and be activated by heat-treatment or by mechanical deformation, for instance by passing the elastic element between a pair of intermeshing corrugated rolls as described in U.S. Pat. No. 5,236,430.

Figure 1:
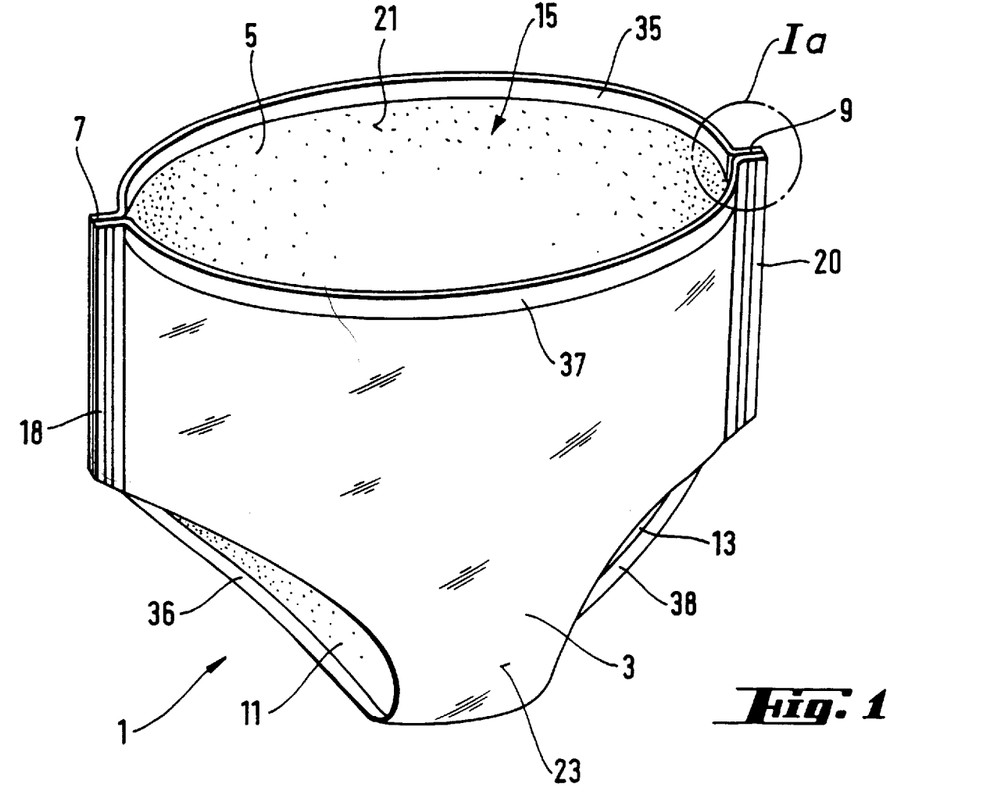
FIG. 1 shows a perspective view of an undergarment having external butt-type side seams.
Figure 1A:
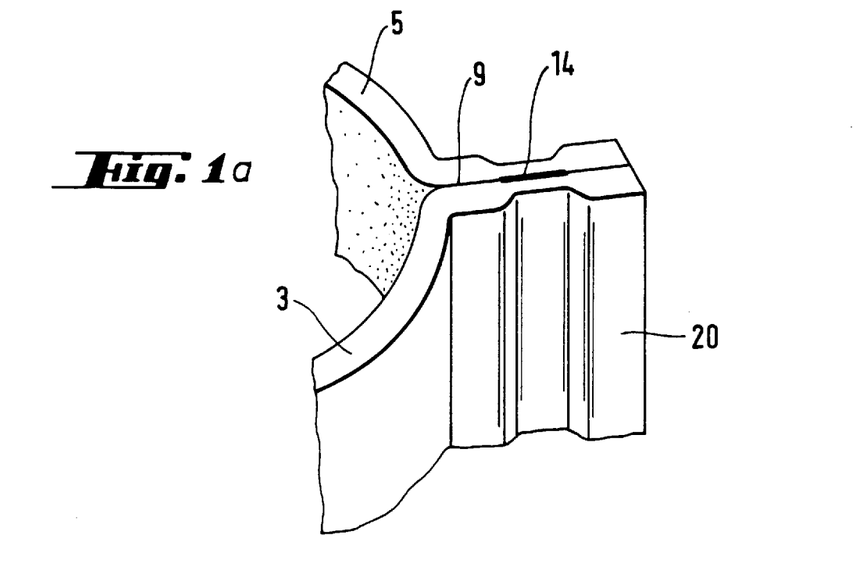

FIG. 1 shows a finished undergarment 1 having a front panel 3 and a back panel 5. The front and back panels are joined together at the area of side seams 7, 9 to form a three-dimensional disposable garment having leg openings 11, 13 and a waist opening 15. The side seams are formed by abutting parts of the front panel 3 and the back panel 5. The waist opening 15 and the leg openings 11,13 are elasticated so that they contract and snugly fit around the waist and legs of a user to provide gasketing seals which prevent liquids from leaking from the garment 1. The side seams 7, 9 may be formed by adhesive bonding, heat sealing, pressure bonding or ultratronic bonding. Preferably the bond region 14 is disposed somewhat inboard of the free edge of the side seams to maintain a soft edge.

The undergarment 1 in FIG. 1 has outwardly located butt-type rims 18,20. The butt-type rims 18,20 are made by folding the preform, or blank, from which the article 1 is formed, along its transverse center line and superimposing the sealing areas that are located on the same surface of the blank in a face-to-face relationship.

The side rims 18 and 20 may alternatively be located on the inside of the undergarment 1. Inner rims can be obtained when the blank of the undergarment is folded along its transverse center line so that its inner, or user-facing surface is facing outwardly upon formation of the seams. Subsequently, by an inverting step, the rims 18 and 20 are turned inwardly.

Figure 2:
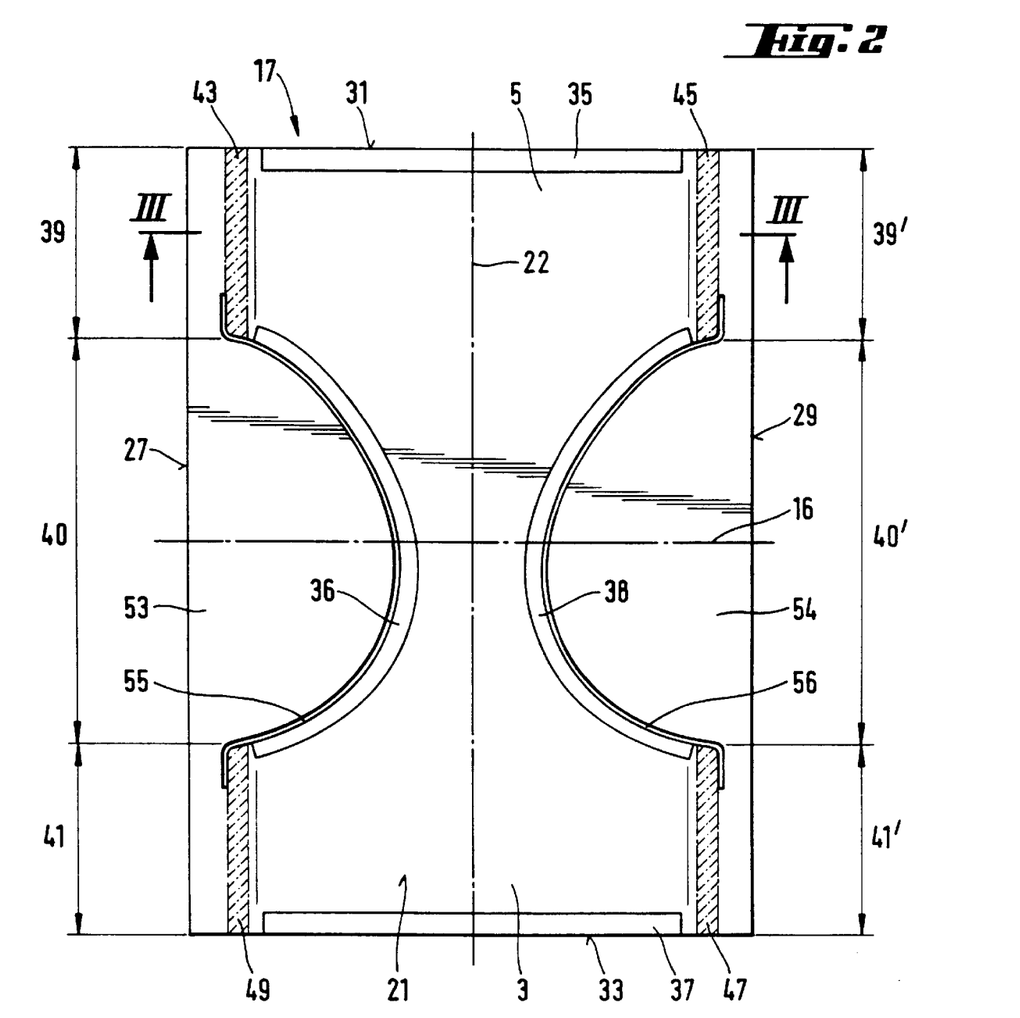
FIG. 2 shows a top plan view of a two-dimensional blank for forming the undergarment of FIG. 1.
Figure 3:
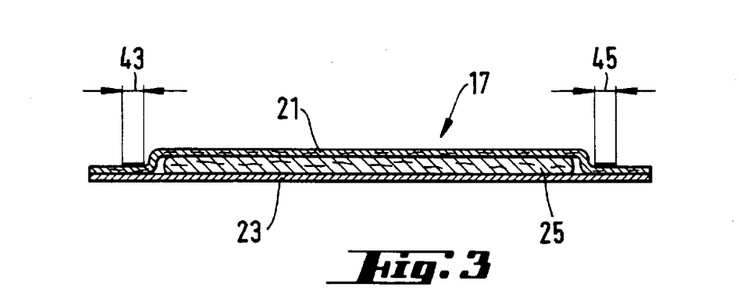
FIG. 3 shows a cross-sectional view of the blank of FIG. 2 along line III—III.

FIG. 2 shows the preform, or blank 17, for forming an absorbent article having side seams in its flattened state. FIG. 3 show a cross-sectional view of the blank 17 along the line III—III of FIG. 2. The blank 17 comprises a liquid-pervious topsheet 21, a liquid-impervious backsheet 23 and an absorbent core 25 interposed between the topsheet and the backsheet. The blank 17 comprises two longitudinal sides 27,29 and two transverse sides 31,33. The longitudinal sides 27,29 and the transverse sides 31,33 form the periphery of the blank 17, which is in this case substantially rectangular. The blank 17 comprises waist elastics 35,37 and leg elastics 36,38. Each longitudinal side 27,29 comprises a back waist section 39,39' and a front waist section 41,41'. For each longitudinal side 27,29 a central section 40, 40' is located between each waist section 39, 41 and 39', 41'. In the area of each waist section a sealing area 43,45,47,49 is comprised. The sealing areas 43–49 are located inboard from the dashed lines in FIG. 2, which dashed lines extend parallel to the waist sections in FIG. 2.

The preform 17 comprises two leg contours 55, 56, which extend generally in the direction of to the longitudinal sides 27,29. The leg contours are formed by cuts through the material of the pre-form 17. The cuts of the leg contours extend through the topsheet 21 and the backsheet 23. The cuts of the leg contours 55, 56 do not extend to the periphery of the blank 17 but stop short in the region of the lower parts of the waist sections 39,39', 41, 41'. The dashed lines at each end of the leg contours 55, 56 are imaginary extensions along which the preform 17 is to be cut after joining the sealing area 43 to sealing area 49 and the sealing area 45 to sealing area 47. The areas of the blank 17 between the leg contours 55,56 and the longitudinal sides 27,29 form gripping flaps 53, 54 by which the blank 17 may be gripped by gripping means.

Figure 4:
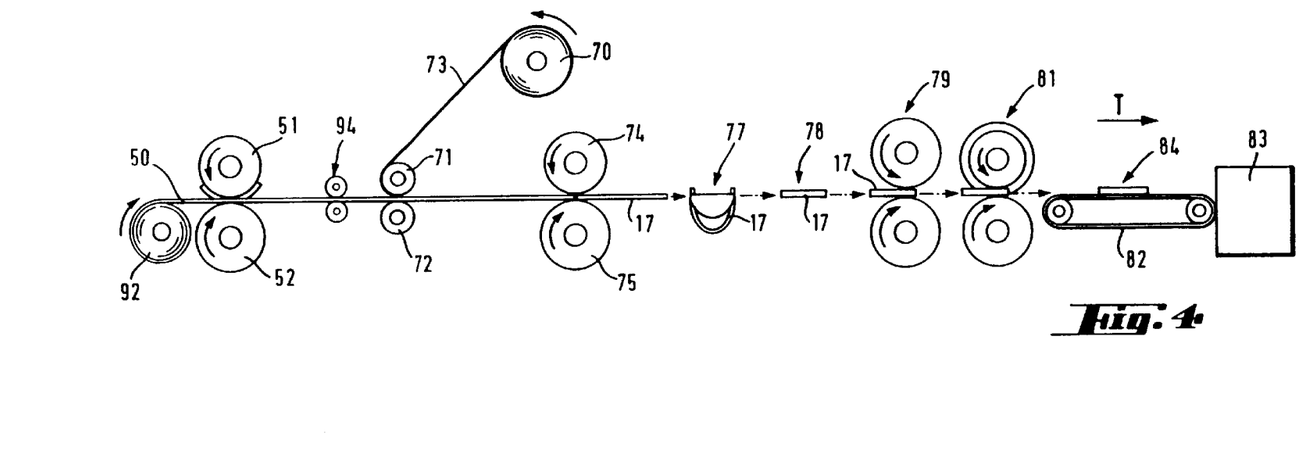
FIGS. 4 and 5 show a schematic side view and a top plan view of a production line for making an undergarment according to the invention, FIG. 6 schematically shows a top plan view of the two-dimensional blank before folding of the blank along the transverse centerline.
Figure 5:
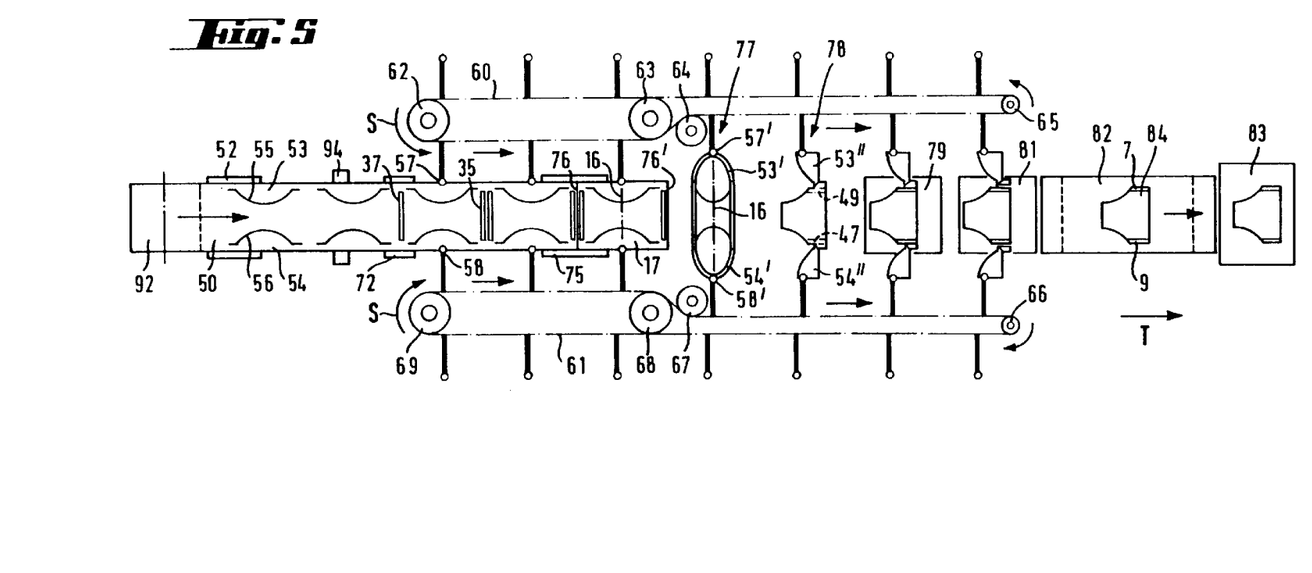

FIGS. 4 and 5 show a schematic side view and top view respectively of a production line for forming an undergarment according to the invention. A continuous web 50 is unwound from a supply roll 92 and is transported in the transport direction T. The web 50 may comprise a single sheet of material or may comprise any of the structures as depicted in FIGS. 14–18.

In case the web 50 comprises a combined liquid impervious topsheet, an absorbent core and a liquid impervious backsheet, the supply roll 92 is absent and web-forming apparatus in present for combining the backsheet, core and topsheet on the upstream side of knife roll 51 and anvill roll 52. This web-forming apparatus has not been depicted. The web 50 passes through the nip of a rotating knife roll 51 and anvill roll 52 which cut the leg contours 55,56 through the web 50. Transport rolls 94 may be provided to support the web 50 and to forward the web 50 in the direction of transport T. Subsequently, the gripping flaps 53, 54 at each side of the web are gripped by grippers 57, 58. The grippers 57, 58 are mounted on an endless belt or chain 60, 61 which extends alongside the web 50 in the direction of transport T. There may also be additional grippers provided which grip the web 50 in the region of the waist sections close to the waist elastics 35,37.

The belts or chains 60, 61 are rotated in the direction of the arrows S around a number of pulleys 62–69 with the same linear velocity as the web 50.

The web 50 is in the example of FIGS. 4 and 5 transported towards the grippers 57,58 in a self-supported fashion, i.e. the web is not supported on a conveyor belt or other transport means. After the grippers 57, 58 engage the gripping flaps 53,54, the waist elastics 35,37 are connected to the web 50. The elastics are supplied from a supply roll 70 and are fed in a pre-stretched state to a combining unit 71,72. In practise, the supply roll 70 will be laterally displaced with respect to the web 50 and the elastics 73 will be fed towards the web 50 in their pre-stretched state in a direction perpendicular to the direction of transport T. The supply roll 70 may alternatively be formed by a box in which the elastic material is festooned.

The combination of the pre-stretched elastic material 73 with the web 50 at the moment when the web is gripped by the grippers 57 and 58, prevents the web from being contracted in the direction perpendicular to the direction of transport T and hence allows accurate process control.

Alternatively, the waist elastics may be applied before the grippers 57,58 engage the web 50. In this case, the outwardly moving grippers counteract the elastic contraction of the waist region and allows the sealing areas of the front and back waist regions to be accurately superimposed.

In a cutting station 74, 75, the continuous web 50 is cut across the width of the web along transverse cut lines 76, 76' to form individual preforms or blanks 17. When the belt or chain 60, 61 on each side of the web 50 passes along the pulleys 63, 64 and 67 68, the distance between the oppositely located grippers 57',58' is increased. By pulling the gripping flaps 53',54' outwardly, the preforms 17 are doubled over along their transverse centerlines 16 and become orientated perpendicularly to the plane of the web 50. This has been indicated at position 77 in FIGS. 4 and 5. Subsequently, the grippers 57',58' are rotated to bring the doubled-over blank 17 back in the plane of the web 50, as indicated at position 78 in FIGS. 4 and 5. In a sealing unit 79, the sealing areas 43,45,47 and 49 are joined.

After the side seams 7 and 9 have been formed, the sealed product passes through a trim knife 81, which cuts off the gripping flaps 53",54" from the sealed side seams. Thereafter, the completed products 84 are transported on a conveyor belt 82 towards a packing station 83.

Figure 6:
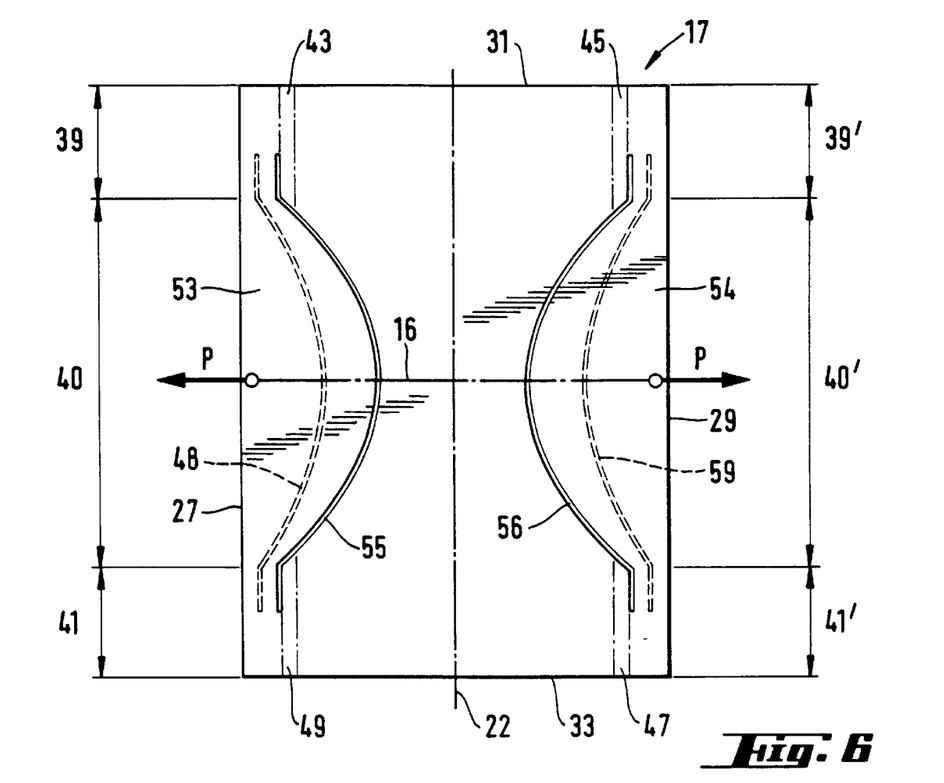

FIGS. 6–9 show the folding operation by which the blank 17 is doubled over along its transverse centerline 16 by pulling the gripping flaps 53,54 in a direction of the arrows P, perpendicularly to the longitudinal sides 27,29. FIG. 6 shows the blank 17 in its flattened state. By pulling the gripping flaps 53,54 of FIG. 6 outwardly in the direction of arrows P, the transverse sides 31, 33 are raised and are rotated towards one another around the transverse centerline 16 such that the blank 17 takes on a U-shaped configuration. There may be a number of additional cuts 48,59 provided, indicated by the dashed lines, to form additional gripping flaps and extending to different points in the front and back waist regions 39,39'; 41,41'. By gripping the additional flaps with additional grippers, the waist sections can be pulled outwardly by the grippers by different amounts, such that for instance a tapered or curved front and back waist section can be obtained, and angled or curved side seams can be formed.

Figure 7:
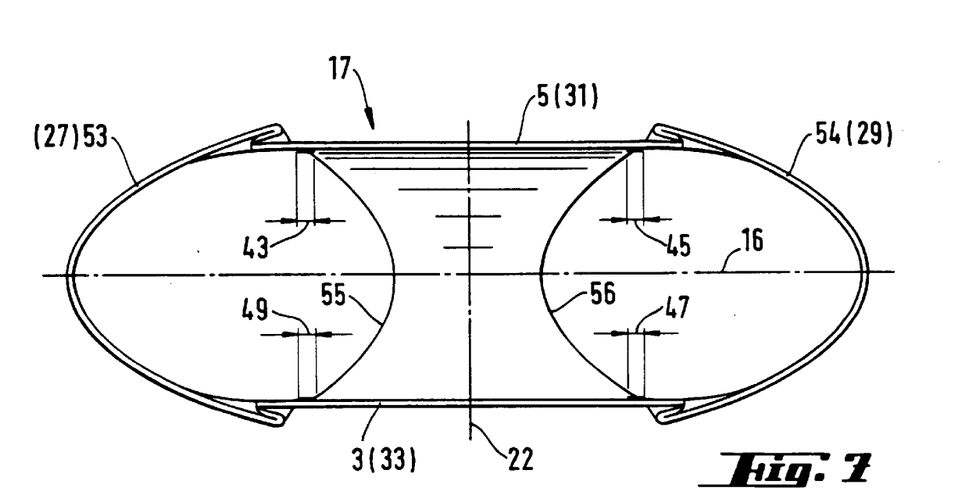
FIG. 7 shows a top plan view of the blank of FIG. 6 after folding of the blank along the transverse centerline.
Figure 8:
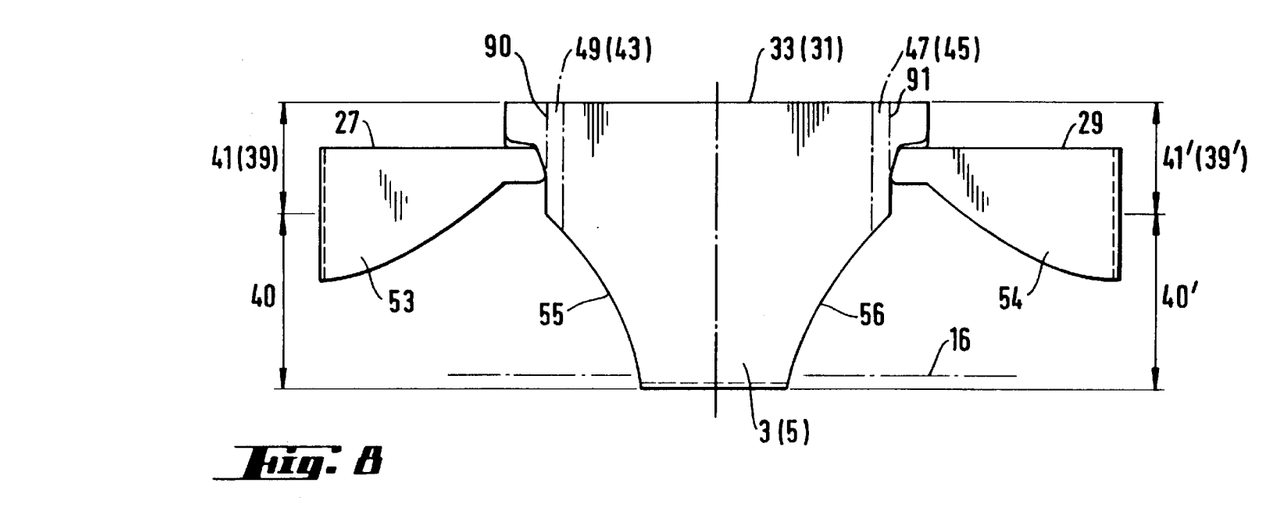
FIG. 8 shows a side elevational view of the configuration of the blank of FIG. 7 from the side of the front panel.

In FIGS. 7 and 8 a top elevational view and a side elevational view of the U-shaped configuration of doubled-over blank 17 are shown respectively. In FIG. 7, the longitudinal centerline 22 and the transverse centerline 16 have the same orientation as the respective centerlines in FIG. 6. In FIG. 8, the longitudinal centerline 22 extends perpendicular to the plane of the drawing. The gripping flaps 53, 54 remain attached to the waist sections 39, 39' and 41, 41' of the blank 17, whereas the gripping flaps in the region of the central sections 40, 40' of the longitudinal sides are pulled outwardly. During the sealing step, the sealing areas 43 and 45 are superimposed on the sealing areas 49 and 47 respectively. After connecting the sealing areas, the gripping flaps 53, 54 are cut off along the lines 90, 91.

Figure 9:
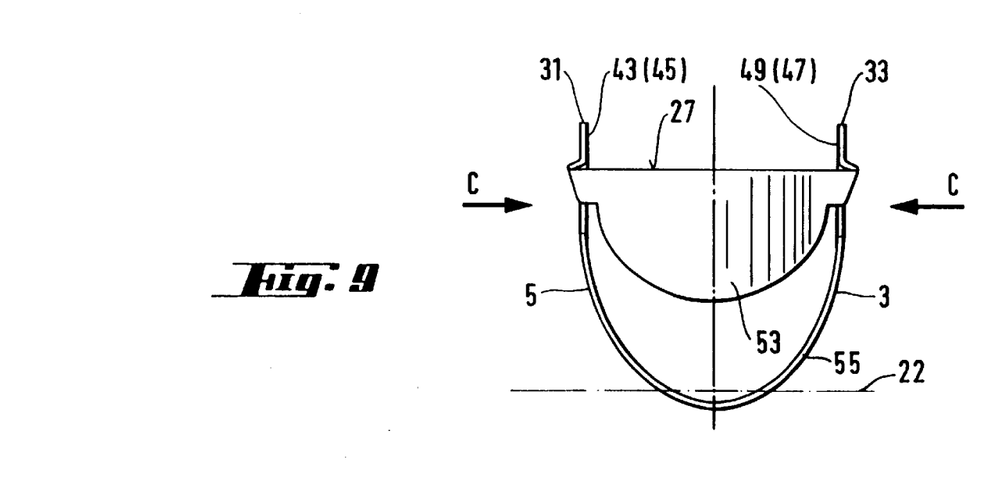
FIG. 9 shows a side elevational view of the configuration of the blank of FIG. 7 from the side of the side seams.

FIG. 9 shows a side elevational view of the u-shaped blank 17, wherein the transverse centerline 16 extends perpendicular to the plane of the drawing. The blank 17 of FIG. 9 is depicted in a configuration prior to reaching the sealing configuration. In the sealing configuration, the sealing areas 43 and 49 are placed in a contacting relationship. The sealing configuration can for instance be reached by passing the blank 17 of FIG. 9 trough a pressure nip and pressing the halves of the doubled over blank together in the direction of the arrows C.

Figure 10:
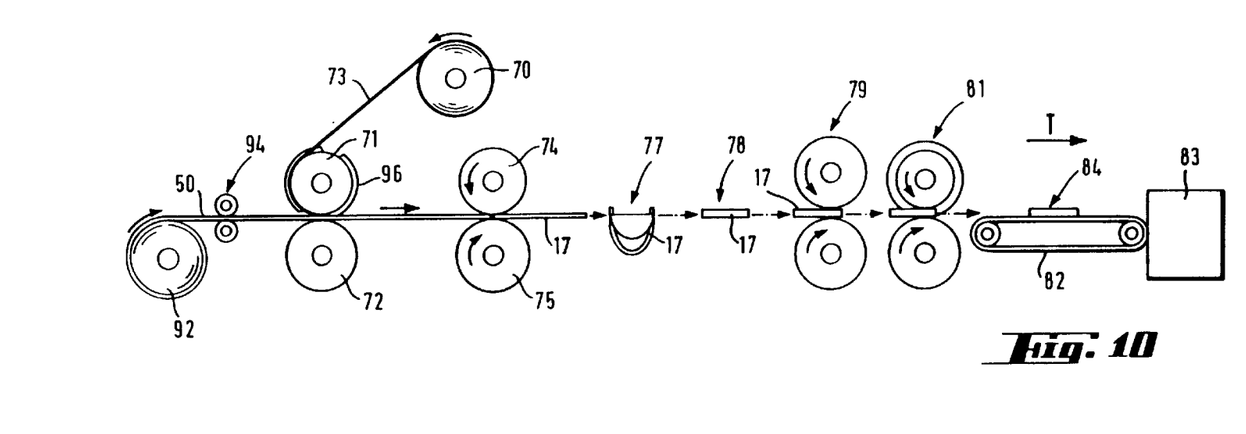
FIGS. 10, 11 and 12, 13 show alternative embodiments of a production line for making an undergarment according to the invention
Figure 11:
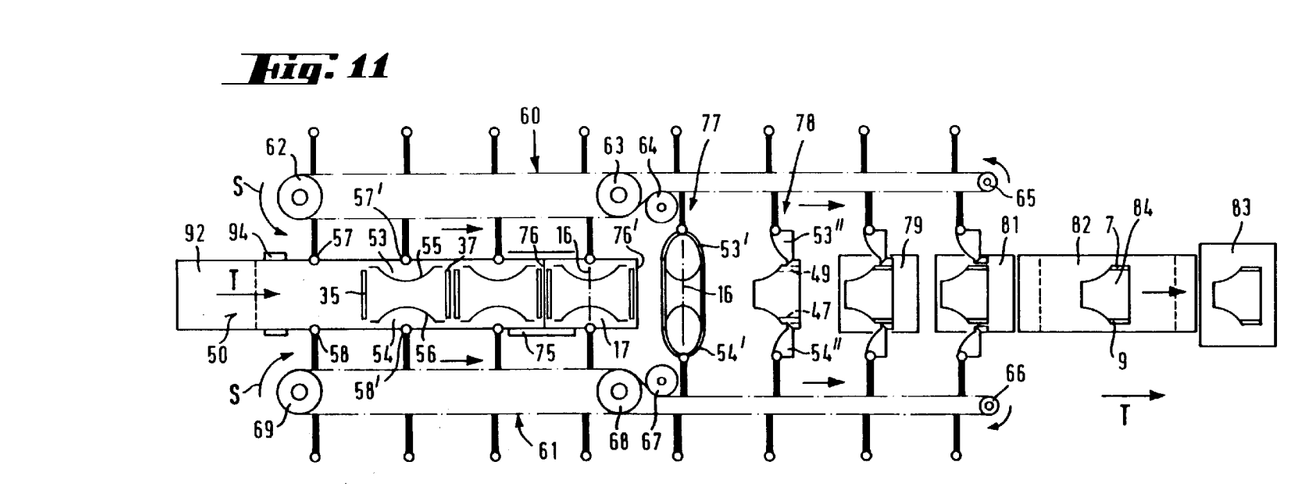

FIGS. 10 and 11 show an embodiment of a production line for carrying out the method according to the invention, wherein in a single applicator-knife unit 71,72 the waist elastics 35,37 are applied and the leg contours 55, 56 are cut. As the grippers 57, 58 engage with the longitudinal edges of the web 50 before the cuts of the leg contours are made, the position of the grippers with respect to the web is accurately determined. By the applicator-knife unit 71, 72, which for instance is formed by a combined rotating knife 96 and a cut-and-slip unit, the first waist elastic 37 is applied to the web. Thereafter, the leg contours 53, 54 are provided, and thereafter the second waist elastic 35 is attached. As the grippers 57, 58 maintain the waist sections of the web in a controlled position, the elastics 35, 37 can be attached in a pre-stretched, or active, state. The waist sections of the web 50 are prevented from contracting by the grippers 57, 58, which pull the waist sections outwardly via the gripping flaps 53, 54. Hence the web 50 is maintained in a flattened state, such that other elements such as a topsheet, elasticated stand-up barrier cuffs or other elements can be accurately placed on the web after providing the waist elastics 35,37.

Figure 12:
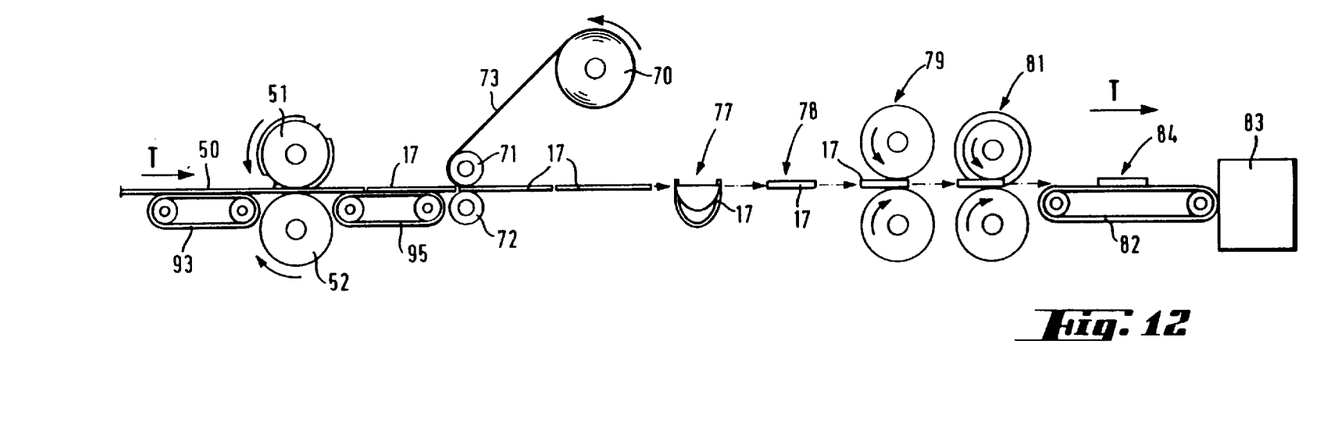
Figure 13:
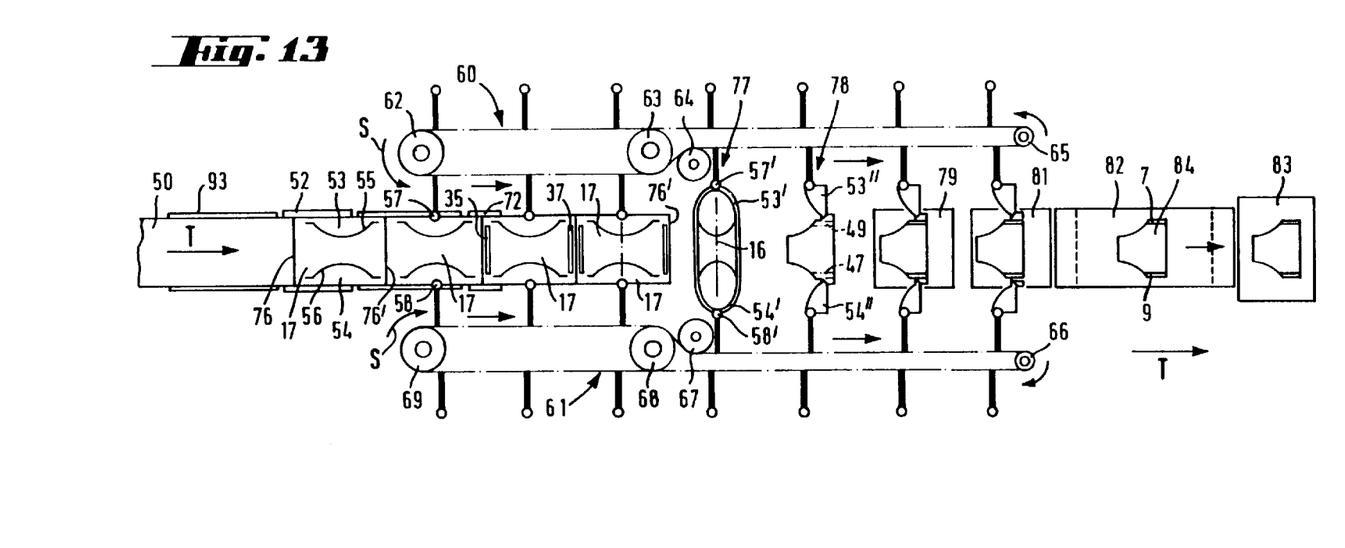

FIGS. 12 and 13 show an embodiment, wherein individual blanks 17 are transported on conveyors 93,95. In this embodiment, the leg contours 55, 56 and the transverse cut lines 76, 76' are both cut by a single knife roll 51 and anvill roll 52. After the leg contours 55, 56 have been provided by the knife and anvill rolls 51,52, the waist elastics 35 and 37 are applied and the gripping flaps 53, 54 are gripped. For the part of the transport trajectory along which the blanks are carried by the grippers 57, 58, the conveyors 93, 95 can be omitted. Alternatively, the conveyors 93, 95 may extend along the entire transport trajectory between the rolls 51, 52 and the packing unit 83, to provide support for the individual blanks, and to prevent the full weight of blanks from being carried by the grippers 57,58.

The sealing unit 79 may comprise and adhesive sealing unit, an ultratronic sealing unit, or any of the known means for connecting the front and back waist panels of the blank 17.

The elastic elements 35, 37 may be "active" elastic elements which are applied in their tensioned state. Alternatively the elastic elements may be applied in their relaxed state and subsequently be activated by heat-treatment or mechanical treatment.

The grippers 57, 58 may be formed by vacuum grippers or by mechanical grippers. Instead of being mounted on a belt or chain running along-side the transport trajectory of the web 50 or blank 17, the grippers may be connected to the same conveyor belt which carries the web or the blanks.

Figure 14:
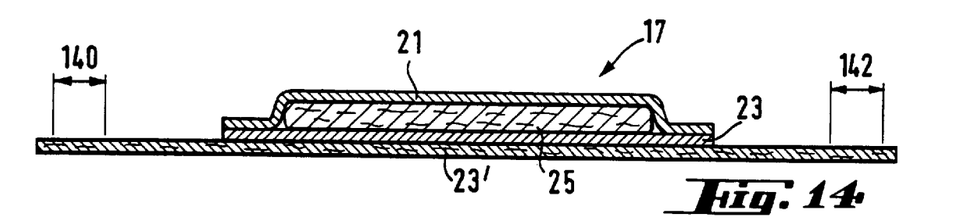
FIGS. 14 to 18 show cross-sectional views of different blanks for making an undergarment according to the invention.
Figure 15:
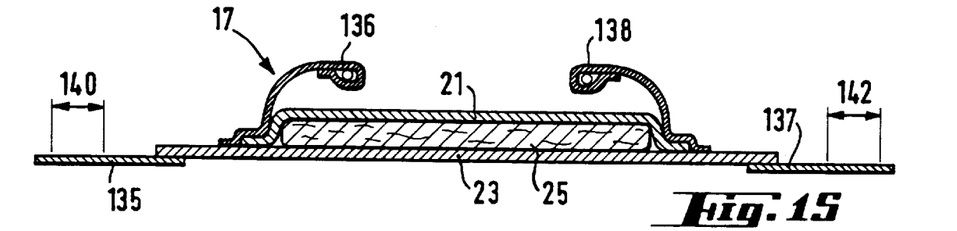
Figure 16:
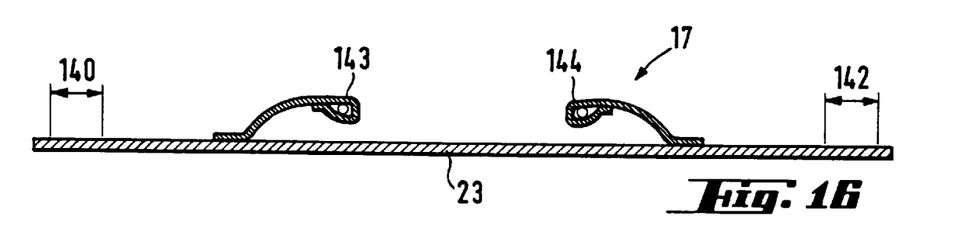

The FIGS. 14–16 show cross-sectional views of different embodiments of blanks for forming an undergarment according to the invention along a line of cross-section running through two sealing areas 140, 142. FIG. 14 shows an embodiment wherein the blank 17 from which the garment is formed comprises a topsheet 21, a dual-layer backsheet 23, 23' and a core 25 interposed between the topsheet and the backsheet. The backsheet is formed by a thermoplastic film 23 and a non-woven outer layer 23'. The thermoplastic film 23 is not coextensive with the non-woven outer layer 23' such that in each side seam only two layers of the non-woven material 23' are comprised. Ventilation and breathability of the absorbent article are obtained through the regions of the non-woven material which are not covered by the impermeable film 23.

In the embodiment of FIG. 15, the blank 17 comprises a thermoplastic backsheet 23 having side panels 135, 137 of stretchable material attached thereto. Furthermore, there may be provided elasticated stand-up cuffs 136,138 on each side of the core 25.

In the embodiment of FIG. 16, the blank 17 forms a re-usable holder for disposable absorbent insert cores, and comprises a non-woven backsheet 23 and two pocket-forming flaps 143,144 below which the insert core can be inserted and which serve to hold the insert core in the proper position with respect to the garment.

Figure 17:
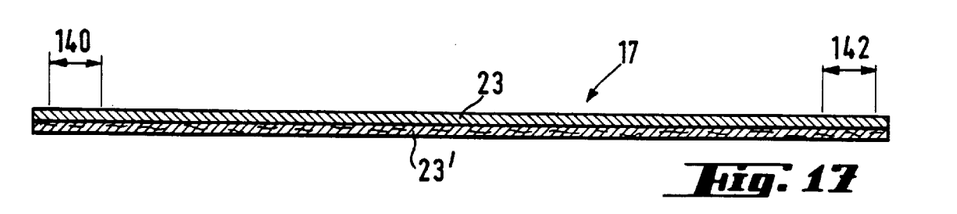

FIG. 17 shows a blank 17 which is made from a laminate of two non-woven layers 23,23' or of a nonwoven layer and a thermoplastic layer, both layers extending into the sealing areas 140,142 for improved strength of the side seams.

Figure 18:
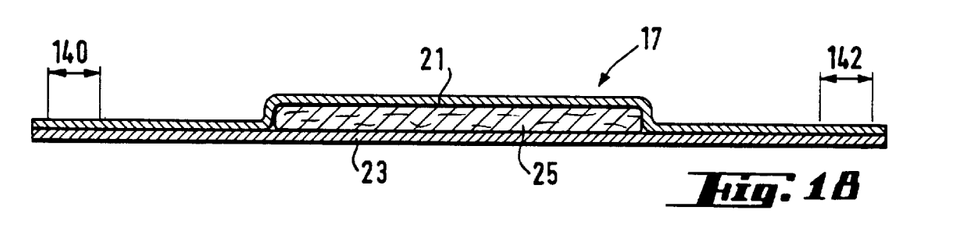

FIG. 18 shows a blank 17 wherein both the topsheet 21 and the backsheet 23 extend into the sealing areas 140, 142 to form reinforced side seams.

The absorbent core 25 of the disposable absorbent article according to the invention may be any absorbent means which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, 'T'-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including conform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying calliper zones, a hydrophilic gradient, a superabsorbent gradient, or lower average density and lower average basis weight acquisition zones; or may comprise one or more layers or structures). The total absorbent capacity of the absorbent core 25 should, however, be compatible with the design loading and the intended use of the absorbent article. Further, the size and absorbent capacity of the absorbent core 25 may be varied to accommodate wearers ranging from infants through adults. Exemplary absorbent structures for use as the absorbent core 25 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

The backsheet 23, 23' is positioned adjacent the garment surface of the absorbent core 25 and is preferably joined thereto by attachment means (not shown) such as those well known in the art. For example, the backsheet 23, 23' may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is, disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23, 23' is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 23, 23' prevents the exudates absorbed and contained in the absorbent core 25 from wetting articles which contact the disposable absorbent article such as bedsheets and undergarments. The backsheet 23, 23' may thus comprise a woven or nonwoven material, polymeric films such as thermoplastic films of polyethylene or polypropylene, or composite materials such as a film-mated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 23, 23' is preferably embossed and/or matte finished to provide a more clothlike appearance. Further, the backsheet 23, 23' may permit vapors to escape from the absorbent core 25 (i.e., breathable) while still preventing exudates from passing through the backsheet 23, 23'.

The topsheet 21 is positioned adjacent the body surface of the absorbent core 25 and is preferably joined thereto and to the backsheet 23, 23' by attachment means (not shown) such as those well known in the art. Suitable attachment means are described with respect to joining the backsheet 23, 23' to the absorbent core 25. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 21 and the backsheet 23, 23' are joined directly to each other in the diaper periphery and are indirectly joined together by directly joining them to the absorbent core 25 by the attachment means (not shown).

The topsheet 21 is compliant, soft feeling, and non-irritating to the wearer's skin. Further, the topsheet 21 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 21 is made of a hydrophobic material to isolate the wearers skin from liquids contained in the absorbent core 25. There are a number of manufacturing techniques which may be used to manufacture the topsheet 21. For example, the topsheet 21 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P8.

Glossary

1 Garment
3 Front panel
5 Back panel
7,9 Side seams
11,13 Leg openings
14 Bond region
15 Waist opening
16 Transverse center line
18,20 Butt-type rims
17 Preform, blank
21 Topsheet
23 Backsheet
25 Core
27,29 Longitudinal sides
31,33 Transverse sides
35,37 Waist elastics
39,39' Back waist section
40,40' Central section
41,41' Front waist section
43,45,47,49 Leg sealing area
48,59 leg contours
50 Web
51 Knife roll
52 Anvill roll
53,54 Gripping flaps
55,56 Leg contours
57,58,57',58' Grippers
60,61 Endless belt/chain
62–69 Pulley
70 Supply roll
71 Transverse cut lines
71,72 Combining unit
73 Elastic
74,75 Cutting station
76,76' transverse cut lines
77,78 Position
79 Sealing unit
81 Trim knife
82 Conveyor belt
83 Packing station
84 Completed products
90,91 Lines
92 Supply roll
93 Peripheral cutting element
94 Transport rolls
135,137 Side panels
136,138 Stand-up cuffs
140,142 Sealing areas

What is claimed is:

1. Method of making an undergarment (1) having side seams (7, 9) from a two-dimensional preform (17), the preform (17) comprising: two longitudinal sides (27, 29), each longitudinal side having a central section (40, 40'), a front waist section (41, 41') and a back waist section (39, 39'), two transverse sides (31, 33), a transverse centerline (16) located midway between the transverse sides (31, 33), and four sealing areas (43, 45, 47, 49) located in the region of the front and the back waist sections (41, 41'; 39, 39'), the method comprising the steps of cutting a continuous web (50) along transverse cut lines (76, 76') to form individual preforms, cutting each preform (17) along a leg contour (55, 56) extending along each longitudinal side (27, 29) in the region of the central section (40, 40'), wherein each leg contour (55, 56) does not touch the respective longitudinal side (27, 29), thus forming two gripping flaps (53, 54), gripping the preform (17) at the gripping flaps (53, 54), pulling the gripping flaps (53, 54) outwardly away from the longitudinal sides (27, 29) such that the preform (17) is doubled over along the transverse centerline (16), placing the sealing areas (43, 45) in the region of the back waist sections (39, 39') in a superimposed relationship with the sealing areas (47, 49) in the region of the front waist sections (41, 41'), and mutually connecting the sealing areas.

2. Method according to claim 1 wherein the preform (17) comprises a liquid pervious topsheet (21), a liquid impervious backsheet (23, 23') and an absorbent core (25) interposed between the topsheet (21) and the backsheet (23, 23'), such that the undergarment forms a disposable absorbent article.

3. Method according to claim 2, wherein the topsheet (21) and the backsheet (23, 23') extend into the sealing areas (43, 45, 47, 49, 140, 142).

4. Method according to claim 1, wherein an elastic element (35, 37) is placed along at least one of the transverse sides (31, 33).

5. Method according to claim 1, wherein an elastic element (35, 37) is placed along each transverse side (31, 33).

6. Method according to claim 5, wherein the elastic element (35, 37) is applied in a pre-stretched form.

* * * * *